United States Patent [19]

Kenessey

[11] 4,151,418
[45] Apr. 24, 1979

[54] MULTIPLE CRYSTAL HOLDER ASSEMBLY FOR WAVELENGTH DISPERSIVE X-RAY SPECTROMETERS

[75] Inventor: Bela Kenessey, Burbank, Calif.

[73] Assignee: Bausch & Lomb, Inc., Rochester, N.Y.

[21] Appl. No.: 825,444

[22] Filed: Aug. 17, 1977

[51] Int. Cl.² .............................................. H01J 37/20
[52] U.S. Cl. .............................. 250/442; 250/277 CH; 250/310
[58] Field of Search ................ 250/276, 277 CH, 310, 250/442

[56] References Cited

U.S. PATENT DOCUMENTS

| 3,391,276 | 7/1968 | Delarue | 250/277 CH |
| 3,536,912 | 10/1970 | Speck | 250/277 CH |
| 3,654,460 | 4/1972 | Payton | 250/277 CH |

Primary Examiner—Craig E. Church
Attorney, Agent, or Firm—Theodore H. Lassagne

[57] ABSTRACT

A novel crystal holder for the wavelength dispersive spectrometers of electron microprobes arranges four crystals as a cylinder segment which may be moved to a position in which it partially encompasses the viewing optics assembly so that low Bragg angle settings may be obtained without mechanical interference, while at the same time the interchanging of crystals by oscillation of the cylinder segment on its axis is possible at any position of the crystal holder.

4 Claims, 9 Drawing Figures

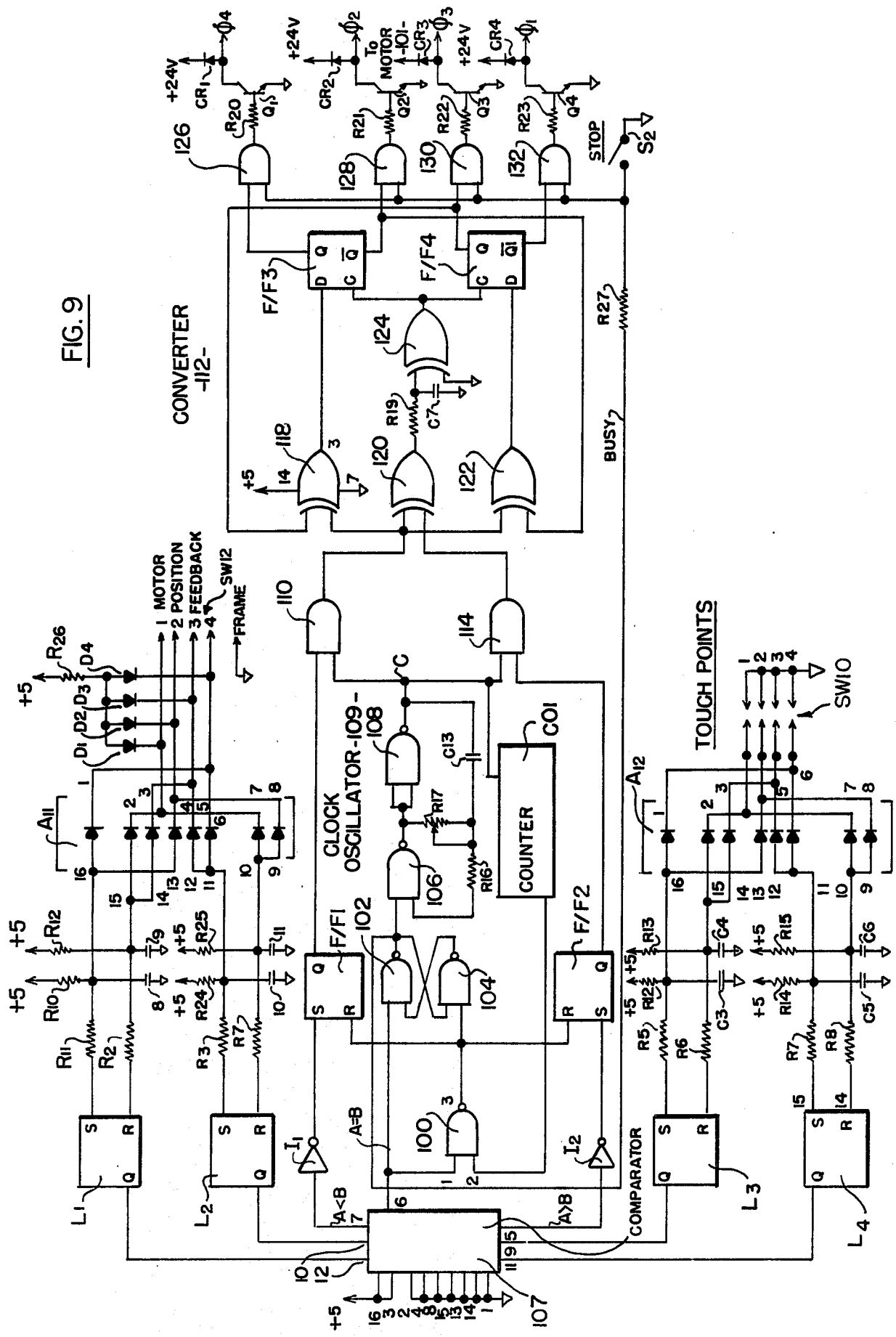

MULTIPLE CRYSTAL HOLDER ASSEMBLY FOR WAVELENGTH DISPERSIVE X-RAY SPECTROMETERS

BACKGROUND OF THE INVENTION

1. Field of the Invention

The present invention relates to improvements in spectrometers for electron probe X-ray analyzers, and more particularly to a novel multi-crystal positioning mechanism for such instruments.

2. Description of the Prior Art

The electron probe microanalyzer is an instrument for X-ray spectrochemical analysis of small areas on the surface of a solid specimen. It consists, basically, of three components: (a) an electron optics system to focus a beam of electrons on the specimen; (b) X-ray optics to analyze the X-rays emitted by the specimen under electron bombardment; and (c) a viewing system such as an optical microscope to aid in the selection of the exact area to be analyzed.

In an instrument of this kind such as that disclosed in the U.S. Pat. of Wittry, No. 3,107,297, the electron optics system and the viewing system are coaxial, and the emergence angle of the X-rays sensed by the X-ray analysis system is maximized in order to provide a desirable line-to-background ratio and to minimize the effects of surface irregularities. The resultant compacting of these components gives rise to special problems in the design of the X-ray optics of such an instrument.

Crystal diffraction, which is used for wavelength dispersion in such an instrument, depends upon the property of a crystal to diffract only particular X-ray wavelengths for each angular setting of the crystal with respect to the X-ray source. As that angle, called the Bragg angle, is changed, the wavelength diffracted will change, but a given crystal refracts efficiently only within a limited Bragg angle range. Therefore, in order to provide for the detection of X-rays within a wide band of the X-ray spectrum, a plurality of crystals of different characteristics, each adapted to efficiently diffract a different portion of the spectrum, is employed.

Since the crystals in such instruments necessarily are located in an evacuated section, various arrangements for effecting an interchange of crystals without breaking the vacuum have been proposed. These have included mounting two crystals on their holders back-to-back so that by a remotely controlled device either may be substituted for the other in analyzing position by rotation of the assembly through a 180° angle. However, two crystals usually are not sufficient to permit the scanning of a sufficient portion of the X-ray spectrum. Therefore, it has been proposed to arrange a larger number of crystals on their holders on the periphery of a cylindrical mounting rotatable under remote control to bring any of the crystals into analyzing position. Such an arrangement, however, limits the angle through which any crystal so mounted may be rocked, since the viewing optics assembly embodied in such apparatus may, in many apparatus configurations, mechanically limit the motion of the crystal holder, preventing rocking of the crystal to as low a Bragg angle as may be desirable.

The primary object of the present invention is to overcome the deficiencies of prior arrangements of this kind and to provide a structure by means of which a series of crystals may be interchanged in analyzing position by remote control while permitting them to be rocked to as low a Bragg angle as desired.

SUMMARY OF THE INVENTION

According to the present invention a crystal holder assembly in the form of a cylinder segment is provided with individual mountings for a plurality of crystals any of which may be moved into analyzing position by rotation of the cylinder segment about its axis.

The crystal holder assembly as a whole is mounted for movement in the same manner as crystal holders of the prior art for the purpose of altering the Bragg angle of any crystal which is in analyzing position at the time. Because the concave portion of the cylinder segment is toward the common axis of the electron optics and the viewing system, regardless of which crystal is in analyzing position, the crystal holder may be brought closer to that axis than has been possible in any prior arrangement, thus, in configurations in which the viewing optics assembly is positioned closely adjacent the magnetic lens objective, making it possible to position any of the four crystals in analyzing position while the crystal holder is positioned so that the crystal in operating position is adjusted to the lowest Bragg angle.

BRIEF DESCRIPTION OF THE DRAWINGS

FIG. 9 is a logic diagram of the stepper motor control circuit.

DESCRIPTION OF THE PREFERRED EMBODIMENT

Figure 1:
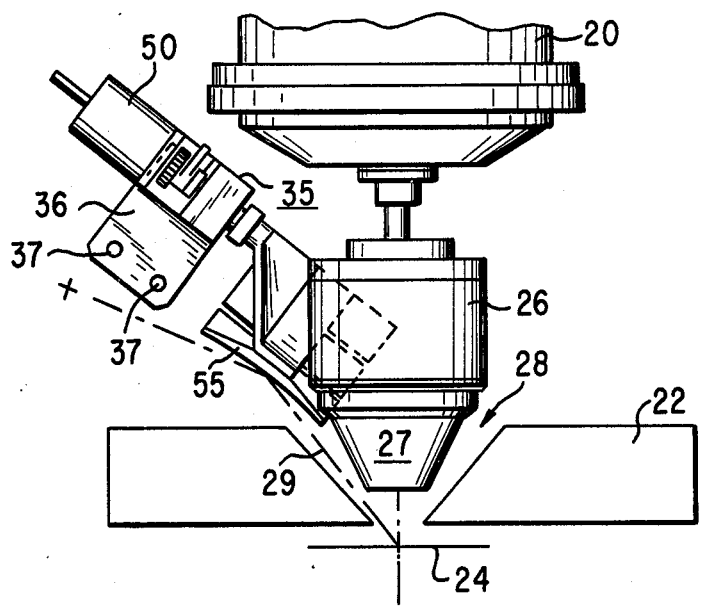
FIG. 1 is a view in side elevation of a crystal holder embodying the invention, showing it in its operating relationship with elements of an electron microprobe X-ray analyzer.
Figure 2:
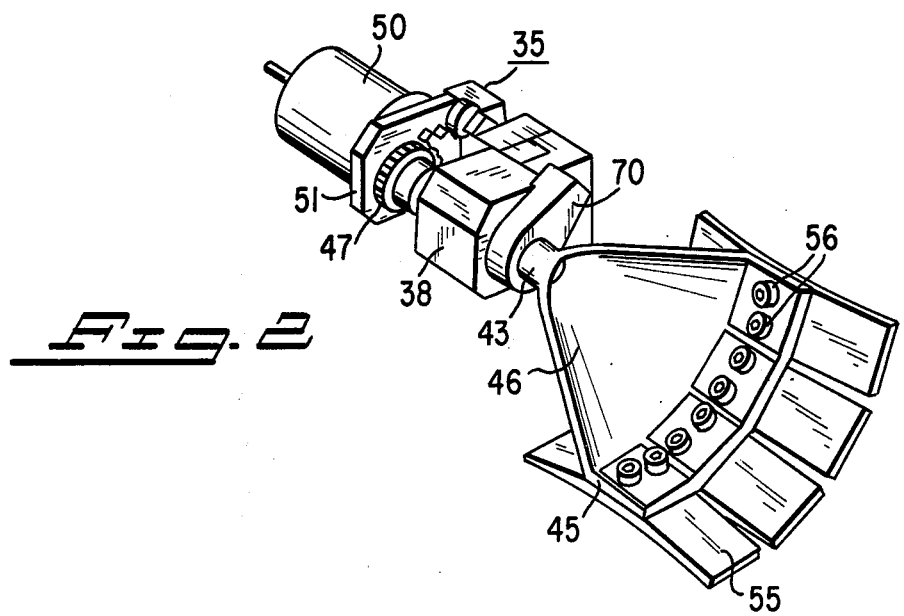
FIG. 2 is a view in perspective of the crystal holder of FIG. 1.

FIG. 1 of the drawing illustrates portions of an instrument manufactured by Applied Research Laboratories Division of Bausch & Lomb, Inc., which is similar to the construction illustrated and described in the U.S. Pat. of Wittry No. 3,107,297. Reference is hereby made to that patent for a disclosure of details not illustrated and described herein.

This instrument comprises a source of electrons generally indicated at 20, together with electron beam focusing means including an objective magnetic lens 22 for focusing electrons from the source into a beam impacting material disposed on a specimen stage the position of which is diagrammatically indicated at 24.

The instrument also includes means for viewing the material being irradiated, including a cylindrical viewing optics assembly 26 coaxial with the electron beam, and in the configuration illustrated having a frusto-conical portion 27 disposed closely adjacent the specimen stage 24 and actually projecting into the gap 28 of the magnetic objective lens 22.

In the operation of this instrument, X-rays emitted by material on the specimen stage 24 in response to irradiation by the electron beam, which emerge along the line 29, pass through the gap 28 and, as described in the above mentioned Wittry patent, are refracted by a crystal along the line 30 to a detector; a linkage such as is illustrated and described in more detail in the U.S. Pat. of Neuhaus No. 3,123,710 being arranged to maintain the proper focal relationship between the specimen, the crystal, and the detector throughout the range of Bragg angle adjustments of the spectrometer.

The crystal holder assembly of the present invention comprises a crystal holder carriage 35 (FIG. 1) designed for mounting as an element of the crystal orienting mechanism of an analyzer such as that illustrated and described in the above mentioned Wittry patent in the same manner as is the single crystal holder illustrated and described in that patent; being movable along a rectilinear path intersecting the electron beam 30 and at the same time rocked upon an axis selected to cause a crystal carried thereon to rock through a Bragg angle in the same manner as does the crystal illustrated and described in the Wittry patent.

Figure 3:
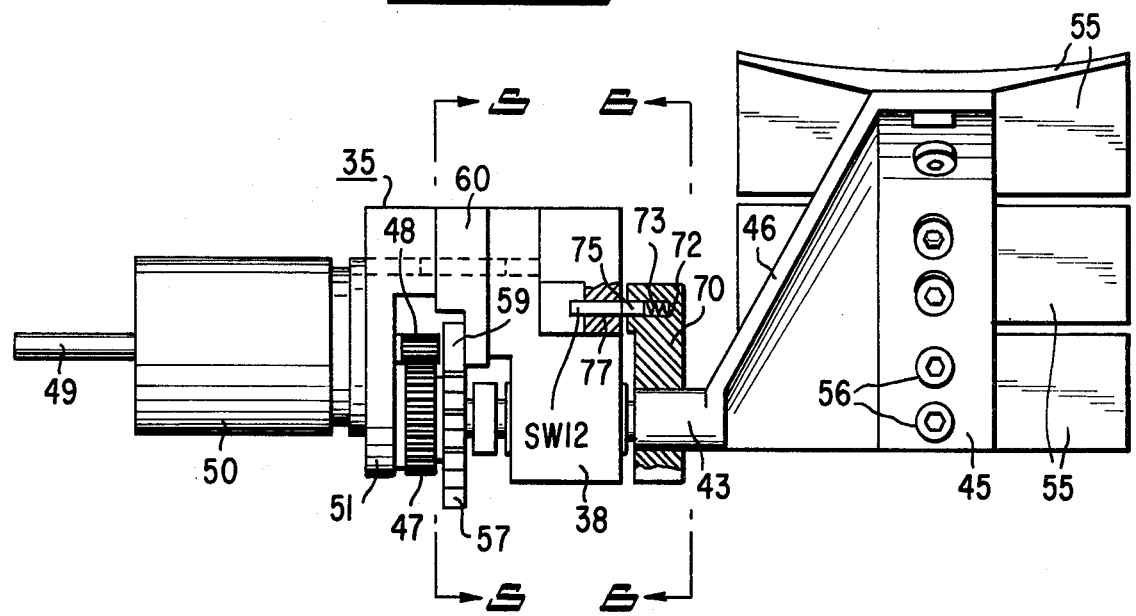
FIG. 3 is a view in plan, partly in section, of the crystal holder of FIG. 1.
Figure 4:
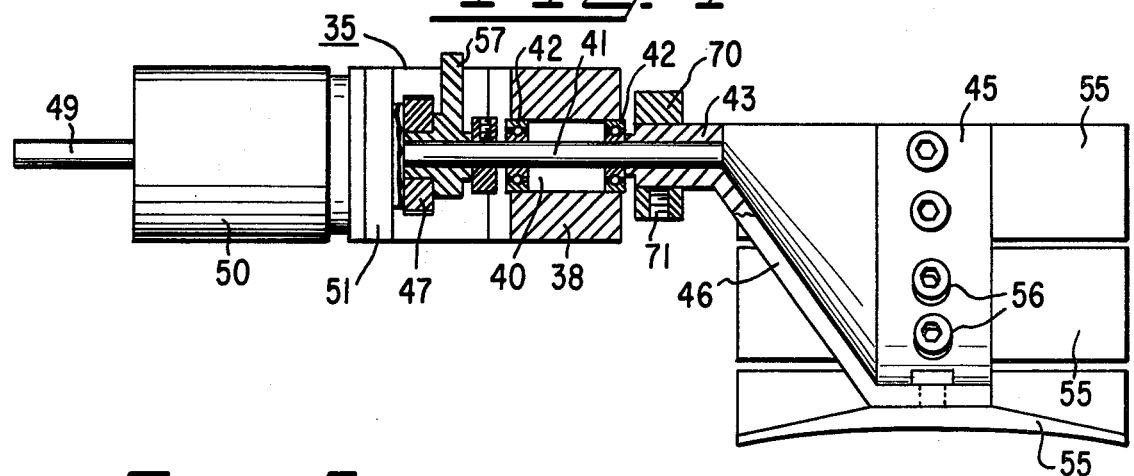
FIG. 4 is a view in side elevation, partly in section, of the crystal holder of FIG. 1.

As shown in FIG. 1, the carriage 35 includes a base 36 provided with spaced mounting holes 37. An extension 38 of the base 36 (see FIGS. 3 and 4) is provided with a bore 40 in which a shaft 41 is rotatably mounted in bearings 42. One end of the shaft 41 extends beyond the base 36 and has secured to it the hub 43 of a cylinder segment 45; a web 46 connecting the hub 43 and segment 45. Secured to the opposite end of the shaft 41 is a gear 47 which meshes with a drive gear 48 fixed to the shaft 49 of a two-phase stepper motor 50 mounted on a flange 51 of base 35.

Mounted on the periphery of the segment 45 are four crystal holders 55, adjustably secured in position by screws 56; crystals (not shown) being adhesively secured to the outer surfaces of the holders 55 as is well known in the art.

Figure 5:
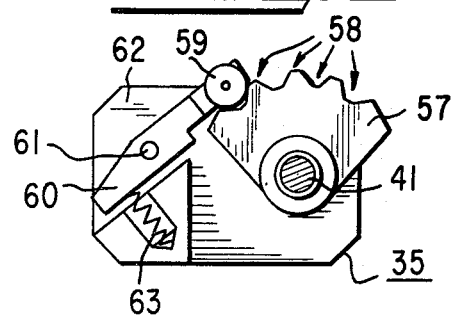
FIG. 5 is a sectional view on the line 5—5 of FIG. 3.

Alignment of any selected one of the crystal holders 55 in operating position is effected by a mechanical detent assembly comprising a segment 57 (see also FIG. 5) fixed to the shaft 41 and provided with notches 58 engageable by a roller 59 rotatably mounted adjacent one end of a lever 60 pivotally mounted at 61 in a notch 62 in base 35; a spring 63 compressed between one end of lever 60 and base 35 urging the roller 59 against segment 57. The angular spacing between the bottoms of the notches 58 is the same as the angular spacing between the centers of crystal holders 55; the arrangement being such that whenever motor 50 is deenergized shaft 41 will be precisely moved into one of four positions; a different one of the crystal holders 55 being operatively positioned in each such position.

Figure 6:
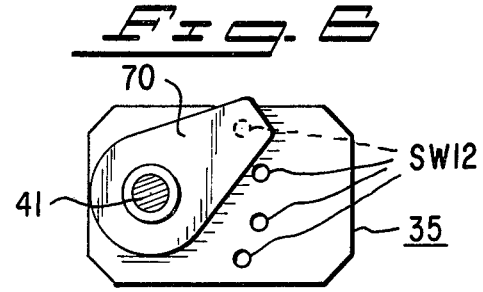
FIG. 6 is a sectional view on the line 6—6 of FIG. 3.

Means are provided for registering the positioning of the crystal holder segment 45 for the purpose of indicating the same and controlling the operation of motor 50 as hereinafter described. This means comprises an arm 70 (see also FIG. 6) secured by a set screw 71 to the hub 43 of segment 45. A recess 72 (FIG. 3) in arm 70 houses a spring 73 compressed between the base of the recess and an electrical contact element 75 slidably mounted in the recess 72. Mounted in insulating sleeves in recesses 77 in base 35 are motor position feedback contacts SW 12 (FIG. 9) the angular spacing of which is the same as the angular spacing of crystal holders 55. This arrangement is such that whenever a crystal holder 55 is in operative position, a corresponding one of the contacts SW 12 will be grounded by engagement with contact 75.

Control means are provided for stepping the crystal holder assembly from any operating position directly to any other operating position upon closure of a circuit designating the desired position.

Figure 7:
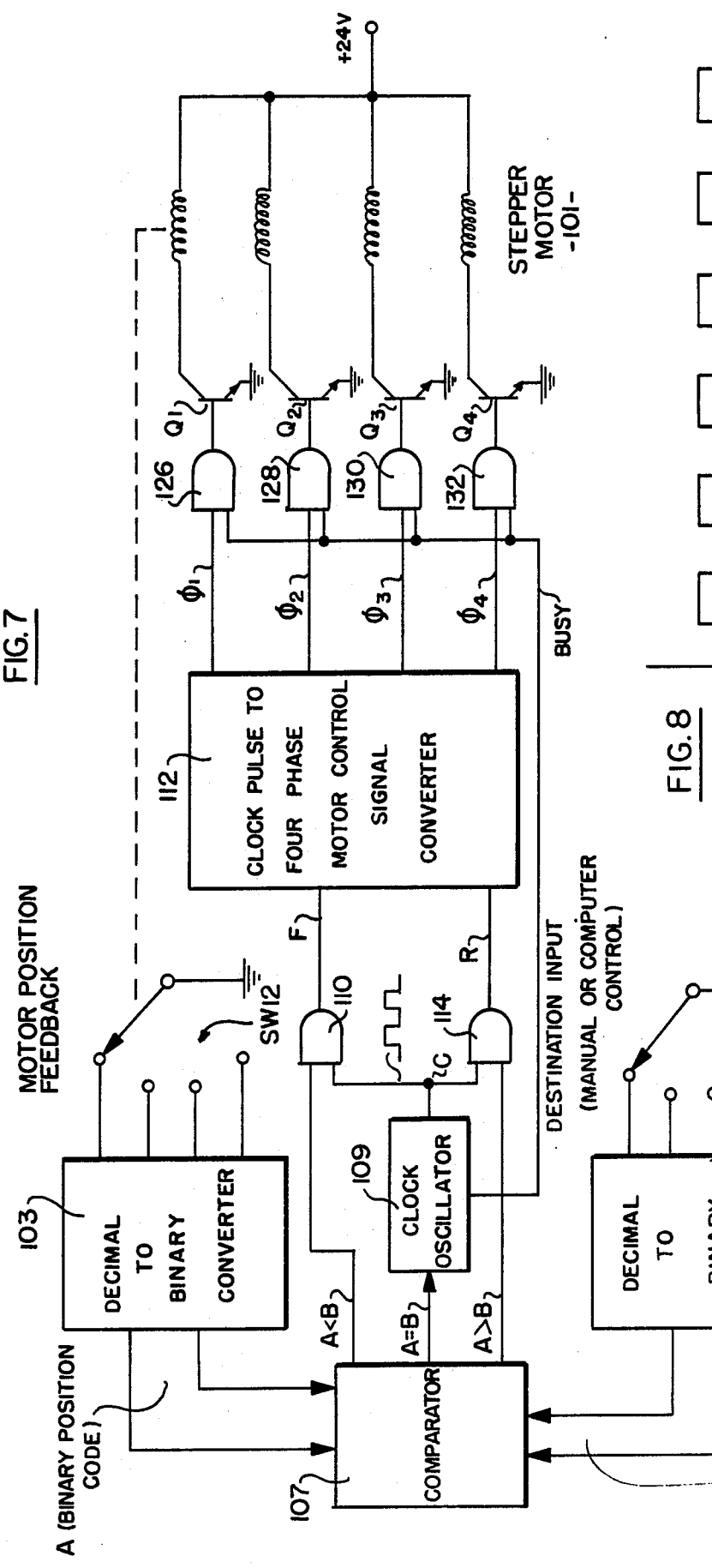
FIG. 7 is a block diagram of the control circuit of the stepper motor.
Figure 8:
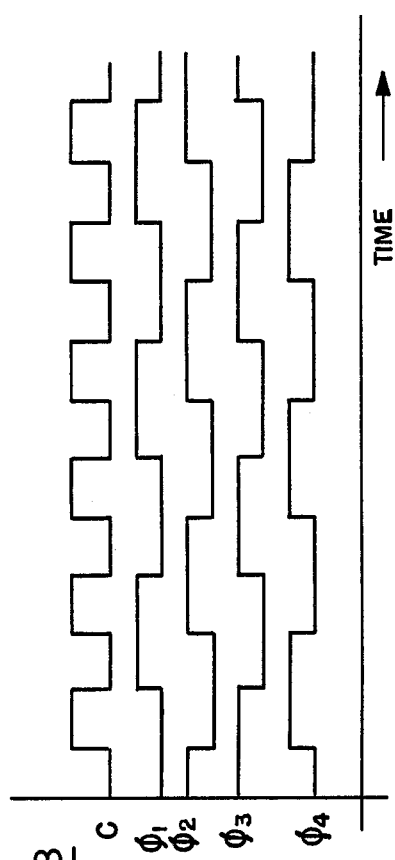
FIG. 8 is a chart of the wave forms applied to the stepper motor.

This means is illustrated in FIGS. 7, 8 and 9. The two-phase synchronous motor 50 is of the type especially designed for stepping applications, where the voltages across the motor windings are square waves, rather than the usual sinusoidal waves. The square waves applied to the stepper motor 101 are shown, for example, by curves $\phi_1$–$\phi_4$ in FIG. 8. The motor may be of the type manufactured by Computer Devices Corporation, Santa Fe Springs, Calif., and sold under the brand name "Rapid-Syn", which has a rating of 0.000012 horse power.

The control means includes a solid state closed-loop digital control circuit which is shown in block form in FIG. 7 and in logic detail in FIG. 9. The control circuit is manually or computer controlled and, in the illustrated embodiment, is capable of causing motor 50 to step from any particular position to another selected position by the shortest angular distance in either a forward direct or a reverse direction.

As shown in the block diagram of FIG. 7, the closed-loop digital control circuit is controlled by a four-position destination switch SW10, which may be either manually or computer controlled; and by a motor position feedback commutator switch SW12 which is mechanically coupled to motor 50, and which steps from one switch contact to another as the motor steps from one angular position to another.

Motor position feedback switch SW12 is connected to a decimal-binary converter 103 which converts the four switch positions of switch SW12 into a two-bit binary position code (A). Destination input switch SW10 is connected to a similar decimal-binary converter 105 which converts the four switch positions of switch SW10 into a two-bit binary destination code (B). The binary outputs from converters 103 and 105 are introduced to a comparator 107. The comparator introduces an output signal to an "and" gate 110 when the binary signal A from converter 103 is less than the binary signal B from converter 105; the comparator 16 introduces an output signal to an "and" gate 114 when the binary signal A from converter 103 is greater than the binary signal B from converter 105; and the comparator 107 introduces an output signal to a clock oscillator 109 when the binary signals A and B from converters 103 and 105 are equal to one another, to stop the operation of the clock oscillator.

When the binary signals from converters 103 and 105 are unequal, the clock oscillator 109 generates clock pulses C, which are shown in FIG. 8. The clock pulses are introduced through the "and" gates 110 and 114 to a converter 112 which converts the clock pulses into the motor control square wave $\phi_1$–$\phi_4$ which are also shown in FIG. 8. The motor control square waves $\phi_1$–$\phi_4$ are introduced through respective "and" gates 126, 128, 130 and 132, and through respective power transistors Q1, Q2, Q3 and Q4, to the windings of the stepper motor 50, which windings are connected to the positive terminal of a 24-volt direct voltage source.

When the binary signal A from converter 103 is less than the binary signal B from converter 105, the motor 50 steps in the forward direction toward its destination, and when the binary signal A is greater than the binary signal B, the motor 50 steps in the reverse direction to its destination. This is achieved by the converter 112, which responds to the clock pulses on either the F lead or on the R lead, to apply the square waves $\phi_1$–$\phi_4$ through the "and" gates 126, 128, 130 and 132, and through the power transistors Q1, Q2, Q3 and Q4, to the field windings of the stepper motor 50. The converter applies the square waves $\phi_1$–$\phi_7$ to the field windings of motor 50, in a particular phase for forward motion of the motor when "and" gate 110 is enabled, and with a particular phase for reverse motion of the motor when "and" gate 114 is enabled.

As the stepper motor 50 steps toward its destination, the motor position feedback switch SW12 moves from one switch contact to the next. When the destination is reached, the binary signal A equals the binary signal B and the clock oscillator 109 stops generating the clock pulses C. When the clock oscillator stops generating clock pulses C, the "and" gates 126, 128, 130 and 132 are disabled, so that the stepper motor 50 is stopped at the destination position. As previously described, the stepper motor includes a mechanical detent assembly, which causes the motor to home-in precisely at its selected destination position, when the stepper motor 50 is de-energized.

In the logic diagram of FIG. 9, the contacts of the motor position feedback switch SW2 are connected through respective light emitter diodes D1, D2, D3 and D4, and through a common 150 ohm resistor R26 to the positive terminal of an appropriate 5-volt direct voltage source. The light emitting diodes provide indications as to the actual angular position of the stepper motor 50 at any particular time. The contacts of the switch SW12 are also connected to a diode array designated A11, which may be an integrated circuit chip of the type presently designated 2719. Pins 15 and 16 of the integrated circuit A11 are connected through respective 10 kilo-ohm resistors R11 and R12 to the S and R input terminals of a latching circuit L1. Pins 15 and 16 are also respectively connected to 100 kilo-ohm resistors R10 and R11 which, in turn, are connected to the positive 5-volt source, and to respective 0.01 microfarad capacitors C8 and C9 which are connected to the frame of the controller unit.

Pins 11, 12 and 9, 10 of integrated circuit A11 are connected through respective 10 kilo-ohm resistors R3 and R4 to the S and R inputs of a latch circuit L2. These pins are also connected to respective 100 kilo-ohm resistors R24 and R25, and to respective 0.01 microfarad capacitors C10 and C11. The resistors are connected to the positive terminal of the 5-volt source, and the capacitors are connected to the frame.

The Q outputs of the latches L1 and L2 are connected to pins 10 and 12 of an integrated circuit which forms comparator 107. The integrated circuit may be of the type designated 4063. Pins 3 and 16 of the integrated circuit are connected to the positive terminal of the 5-volt source, and pins 1, 2, 4, 8, 13, 14 and 15 are connected to the frame.

The switch SW 10 is connected to a diode array A12 which, likewise, may be an integrated circuit of the type designated 2719. Pins 16 and 14, 15 of the integrated circuit are connected through respective 1 megohm resistors R5 and R6 to the S and R inputs of a latch L3, and pins 11 and 9–10 are connected through respective 1 megohm resistors R7 and R8 to the S and R inputs of a latch L4. Pins 16 of the integrated circuit A12 is connected to the junction of a 10 megohm resistor R12 and 0.01 microfarad capacitor C3, and pins 14, 15 are connected to the junction of a 10 megohm resistor R12 and a 0.01 microfarad capacitor C4. Likewise, pins 11 and 12 are connected to the junction of a 10 megohm resistor R14 and 0.01 microfarad capacitor C5, and pins 9, 10 are connected to the junction of a 10 megohm resistor R15 and 0.01 microfarad capacitor C6. The resistors are connected to the positive terminal of the 5-volt source, and the capacitors are connected to the frame.

The latches L1, L2, L3 and L4 may all be included in a single integrated circuit of the type presently designated 4044. The Q outputs of the latches L3 and L4 are respectively connected to pins 9 and 11 of comparator integrated circuit 107.

The latches L1, L2 and diode array A11 in FIG. 9 constitute the decimal-binary converter 103 of FIG. 7; and the latches L3, L4 and diode array A12 in FIG. 9 constitute the decimal-binary converter 105 of FIG. 7. When the binary signal A is less than binary signal B, an output appears at pin 7 of comparator 107, and this output is introduced through an inverter I1 to the S input of a flip-flop F/F1. When the binary signal A is greater than binary signal B, an output appears at pin 5 of integrated circuit 107, and this output is introduced through an inverter I2 to the S input of a flip-flop F/F2. When the binary signal A equals the binary signal B, an output appears at pin 6 of comparator 16, and this latter output is introduced to a set-reset flip-flop composed of "nand" gates 102, 104 and to one of the input terminals of a "nand" gate 100. The output of "nand" gate 100 resets the flip-flops F/F1 and F/F2, and the last-named output also resets the flip-flop formed by the "nand" gates 102, 104.

The clock oscillator 109 is formed by two "nand" gates 106, 108, the output of "nand" gate 108 being coupled back to one of the inputs of "nand" gate 106 through a 1 microfarad capacitor C13 and through a 1.5 megohm resistor R16. The output of "nand" gate 106 is connected to the inputs of "nand" gate 108, the latter "nand" gate being connected as an inverter, and these connections are connected to a 500 kilo-ohm potentiometer R17 which, in turn, is connected to the junction of resistor R16 and capacitor C13. The clock oscillator introduces clock pulses C to "and" gates 110 and 114. The clock oscillator 109 generates the clock pulses C so long as the set-reset flip-flop 102, 104 is reset. The output of the clock oscillator is also introduced to a binary counter C01 which is connected, for example, to count to eight, and then to reset itself to zero. The output of counter C01 is introduced to the other input terminal of "nand" gate 100.

The output of "and" gate 110 is connected to one of the input terminals of each of a series of exclusive "or" gates 118, 120, 122. The output of "and" gate 114 is connected to the other input terminal of exclusive "or" gate 120. The exclusive "or" gates 118, 120, 122, together with a further exclusive "or" gate 124 (which is connected as an inverter) may be contained on an integrated circuit chip of the type presently designated 4070. Exclusive "or" gate 118 is connected to the E input of a flip-flop F/F3, and exclusive "or" gate 122 is connected to the D input of a flip-flop F/F4. Exclusive "or" gate 120 is connected through a 1 kilo-ohm resistor R19 to one input of exclusive "or" gate 124, the other input of which is connected to the frame. Resistor R19 is also connected to the frame through a 0.01 microfarad capacitor C7. The output of exclusive "or" gate 124 is connected to the C inputs of flip-flops F/F3 and F/F4.

The Q output of flip-flop F/F3 is connected to "and" gate 126, the Q output of flip-flop F/F3 is connected to "and" gate 128 and to the second input terminal of exclusive "or" gate 122. The Q output of flip-flop F/F4 is connected to "and" gate 130 and to the second input terminal of exclusive "or" gate 118, and the Q output of flip-flop F/F4 is connected to "and" gate 132. The Q output of the set-reset flip-flop 102, 104 is also connected by a "busy" line, through a 10 kilo-ohm resistor R27, to the second input terminals of "and" gates 126, 128, 130 and 132. Resistor R27 is also connected to a stop switch S2, whose movable arm connects with the frame.

The "and" gates 126, 128, 130 and 132 are connected to the respective power transistors Q1, Q2, Q3 and Q4 through respective 10 kilo-ohm resistors R20, R21, R22 and R23. The power transistors $Q_1$–$Q_4$ may be of the type designated 2N6044. The emitters of the power transistors are connected to the frame, and the collectors are connected to the respective motor windings $Q_1$–$Q_4$, and through respective diodes CR1 and CR2, CR3 and CR4 to the positive terminal of a 24-volt direct voltage source.

In the operation of the circuit of FIG. 9, when the binary signal A is not equal to the binary signal B, clock oscillator 109 generates clock pulses C, and introduces the clock pulses to the "and" gates 110 and 114. If the binary signal S is less than the binary signal B, flip-flop F/F1 is set, so that "and" gate 110 is enabled, and if binary signal A is greater than binary signal B, flip-flop F/F2 is set, so that "and" gate 114 is enabled. When "and" gate 110 is enabled, the flip-flops F/F3 and F/F4 are operated to generate the four square waves Q1, Q2, Q3 and Q4 with a particular phase so that motor 50 is stepped in its forward direction toward a selected destination position. On the other hand, when flip-flop F/F2 is set, the flip-flops F/F3 and F/F4 are caused to generate the four square waves with a timing such that the motor 50 is driven in its reverse direction toward the selected destination.

In the illustrated embodiment, eight clock pulses C are required to step motor 50 from one position to the next. The counter CO1 produces an output for the eighth clock pulse, which is introduced to "nand" gate 100. The "nand" gate 100, however, is disabled until the desired destination is reached, at which time binary signal A equals binary signal B. When that occurs, the output pulse from counter CO1 is passed by "nand" gate 100 to the set input terminal of set-reset flip-flop 102, 104 to set that flip-flop so as to stop clock oscillator 109, and also to reset flip-flops F/F1 and F/F2. When flip-flop 102, 104 is set, the busy line immediately disables the "and" gates 126, 128, 130 and 132 to stop the motor. The motor also can be stopped at any position by closing stop switch S2 which immediately disables the "and" gates 126, 128, 130 and 132.

I claim:

1. An electron probe X-ray analyzer having a specimen stage; a source of electrons; means for focusing electrons from said source into a beam impacting material disposed on said stage including an objective magnetic lens having a gap; a cylindrical optical viewing assembly coaxial with the electron beam path and having a conical portion extending within the gap of the magnetic objective lens; a crystal orienting mechanism including means for moving a crystal along a path at an acute angle to the electron beam path for varying the Bragg angle of said crystal and a crystal holder comprising a base member adapted to be secured to said crystal orienting mechanism, a shaft rotatably mounted on said base member, a cylinder segment carried by said shaft coaxially therewith and having a concave portion movable into partially encompassing relationship with said viewing optics assembly, a plurality of crystal holders mounted on the convex surface of said cylinder segment and a stepping motor carried by said base and driving said shaft.

2. A crystal holder assembly according to claim 1 including means for individually adjusting the positioning of each of said crystal holders on said cylinder segment.

3. A crystal holder assembly according to claim 1 including means for aligning said cylinder segment in predetermined spaced rotational positions whereby any selected one of said crystal holders may be precisely brought to a desired operating position.

4. A crystal holder assembly according to claim 1 including a series of electrical contact elements carried by said base member and a complementary movable contact element operable by said shaft to engage one of said series of contacts as each of said crystal holders is brought to a predetermined position by rotation of said shaft.

* * * * *